United States Patent
Trini et al.

(10) Patent No.: US 11,950,947 B2
(45) Date of Patent: Apr. 9, 2024

(54) GENERATION OF COMPOSITE IMAGES BASED ON LIVE IMAGES

(71) Applicant: Siemens Healthcare GmbH, Erlangen (DE)

(72) Inventors: Martin Trini, Fürth (DE); Darshan Metha, Gilberts, IL (US)

(73) Assignee: Siemens Healthineers AG, Erlangen (DE)

( * ) Notice: Subject to any disclaimer, the term of this patent is extended or adjusted under 35 U.S.C. 154(b) by 406 days.

(21) Appl. No.: 16/756,512

(22) PCT Filed: Oct. 30, 2018

(86) PCT No.: PCT/EP2018/079714
§ 371 (c)(1),
(2) Date: Apr. 16, 2020

(87) PCT Pub. No.: WO2019/086457
PCT Pub. Date: May 9, 2019

(65) Prior Publication Data
US 2020/0281554 A1 Sep. 10, 2020

Related U.S. Application Data

(60) Provisional application No. 62/580,589, filed on Nov. 2, 2017, provisional application No. 62/580,598, filed (Continued)

(51) Int. Cl.
*A61B 6/00* (2006.01)
*A61B 6/42* (2024.01)
(Continued)

(52) U.S. Cl.
CPC .......... *A61B 6/5241* (2013.01); *A61B 6/4208* (2013.01); *A61B 6/463* (2013.01);
(Continued)

(58) Field of Classification Search
CPC .............................. A61B 6/5241; G06T 19/00
See application file for complete search history.

(56) References Cited

U.S. PATENT DOCUMENTS

| 7,415,095 B2 | 8/2008 | Wofford et al. |
| 9,414,799 B2 * | 8/2016 | Mistretta ................... G06T 5/50 |

(Continued)

FOREIGN PATENT DOCUMENTS

| CN | 1535657 A | 4/2004 |
| CN | 101082991 A | 12/2007 |

(Continued)

OTHER PUBLICATIONS

Gering D T et al: "An Integrated Visualization System for Surgical Planning and Guidance Using Image Fusion and an Open MR11" Journal of Magnetic Resonance Imaging, Society for Magnetic Resonance Imaging, Oak Brook, IL, US, vol. 13, 2001, pp. 967-975.

(Continued)

*Primary Examiner* — Angela M Hoffa
*Assistant Examiner* — Younhee Choi

(57) ABSTRACT

A system and method includes determination of a projection axis associated with the two-dimensional projection image, generation of a second two-dimensional image from the three-dimensional image based on the projection axis, registration of the two-dimensional projection image with the second two-dimensional image, combination of the registered two-dimensional projection image with the three-dimensional image in a plane of the three-dimensional image substantially orthogonal to the projection axis, and display of the combined image.

15 Claims, 14 Drawing Sheets

Related U.S. Application Data on Nov. 2, 2017, provisional application No. 62/580,586, filed on Nov. 2, 2017.

(51) Int. Cl.
  *A61B 6/46* (2024.01)
  *G06T 19/00* (2011.01)
(52) U.S. Cl.
  CPC .............. *A61B 6/466* (2013.01); *A61B 6/469* (2013.01); *G06T 19/00* (2013.01)

(56) References Cited

U.S. PATENT DOCUMENTS

| | | |
|---|---|---|
| 2003/0181809 A1 | 9/2003 | Hall et al. |
| 2007/0055131 A1* | 3/2007 | Deinzer ................. A61B 5/416 600/407 |
| 2007/0297565 A1 | 12/2007 | Wofford et al. |
| 2008/0037843 A1 | 2/2008 | Fu et al. |
| 2010/0111389 A1 | 5/2010 | Strobel et al. |
| 2010/0201708 A1* | 8/2010 | Dresel ....................... G06T 5/50 345/158 |
| 2010/0296623 A1 | 11/2010 | Mielekamp et al. |
| 2011/0033026 A1 | 2/2011 | Ulrici et al. |
| 2011/0069063 A1 | 3/2011 | Liao et al. |
| 2012/0006356 A1 | 3/2012 | Klingenbeck |
| 2013/0101084 A1* | 4/2013 | Shimizu ................. A61B 6/487 378/42 |
| 2013/0113802 A1* | 5/2013 | Weersink ............. A61N 5/1065 345/427 |
| 2013/0336565 A1* | 12/2013 | Bakker ..................... G06T 7/30 382/131 |
| 2014/0328462 A1* | 11/2014 | Uehara ................ A61B 6/5288 378/62 |
| 2015/0100290 A1* | 4/2015 | Falt ........................ G16H 50/50 703/2 |
| 2015/0332508 A1 | 11/2015 | Jovanovic |
| 2016/0005168 A1 | 1/2016 | Merlet |
| 2016/0292818 A1* | 10/2016 | Sakamoto ............. G09G 5/373 |
| 2016/0335777 A1 | 11/2016 | Borsdorf et al. |
| 2018/0161099 A1* | 6/2018 | Dumenil ................ G06T 19/20 |
| 2021/0077047 A1* | 3/2021 | Tolkowsky ............ G06N 20/00 |

FOREIGN PATENT DOCUMENTS

| | | | |
|---|---|---|---|
| DE | 102013208897 A1 * | 11/2014 | .......... A61B 5/0073 |
| KR | 20100054973 A | 5/2010 | |

OTHER PUBLICATIONS

European Search Report dated Mar. 21, 2019 for PCT Application No. EP2018079714 , pp. 1-8.

Comer, A. J., et al. "Characterising the behaviour of composite single lap bonded joints using digital image correlation." International Journal of Adhesion and Adhesives 40 (2013): 215-223.

Jia, Ji, Zheng Qin, and Jiang Lu. "A method for 3D Model Retrieval Using Grid Decomposition of Boundary Vertexes of 2D Projection." Chinese Journal of Computers-Chinese Edition—29.12 (2006): 2119.

* cited by examiner

GENERATION OF COMPOSITE IMAGES BASED ON LIVE IMAGES

CROSS-REFERENCE TO RELATED APPLICATIONS

The present application claims priority to U.S. Provisional Application Ser. No. 62/580,586, filed Nov. 2, 2017, U.S. Provisional Application Ser. No. 62/580,598, filed Nov. 2, 2017, and U.S. Provisional Application Ser. No. 62/580,589, filed Nov. 2, 2017, the contents of which are herein incorporated by reference for all purposes.

BACKGROUND

Medical imaging systems are used to acquire images of patient volumes. A radiologist may use these images to diagnose disease and plan treatment thereof. During treatment, a physician may wish to review an image which was used to plan the treatment. Moreover, additional images may be acquired during treatment and reviewed in conjunction with the planning image in order to guide treatment.

Conventionally, the review of in-treatment (i.e., live) images in conjunction with planning images is problematic. The planning image is often a three-dimensional image, or a slice thereof, and the live image is a two-dimensional (e.g., projection) image. Accordingly, conventional systems display, at best, a two-dimensional live image as a static background to a three-dimensional planning image having a fixed orientation.

Systems are therefore desired to coherently display a live two-dimensional image along with a pre-acquired three-dimensional image. Systems are also desired to integrate the two-dimensional image and the three-dimensional image based a region of interest defined by the system or by a user.

Some current imaging systems display a matrix of images including a three-dimensional image and three orthogonal multiplanar reconstructions (MPRs) generated based on the three-dimensional image. Integration of a live image with one or more images of this matrix is desirable. Also desired are systems which update the matrix of images based on characteristics of the live image.

BRIEF DESCRIPTION OF THE DRAWINGS

The construction and usage of embodiments will become apparent from consideration of the following specification as illustrated in the accompanying drawings, in which like reference numerals designate like parts, and wherein.

DETAILED DESCRIPTION

Figure 1:
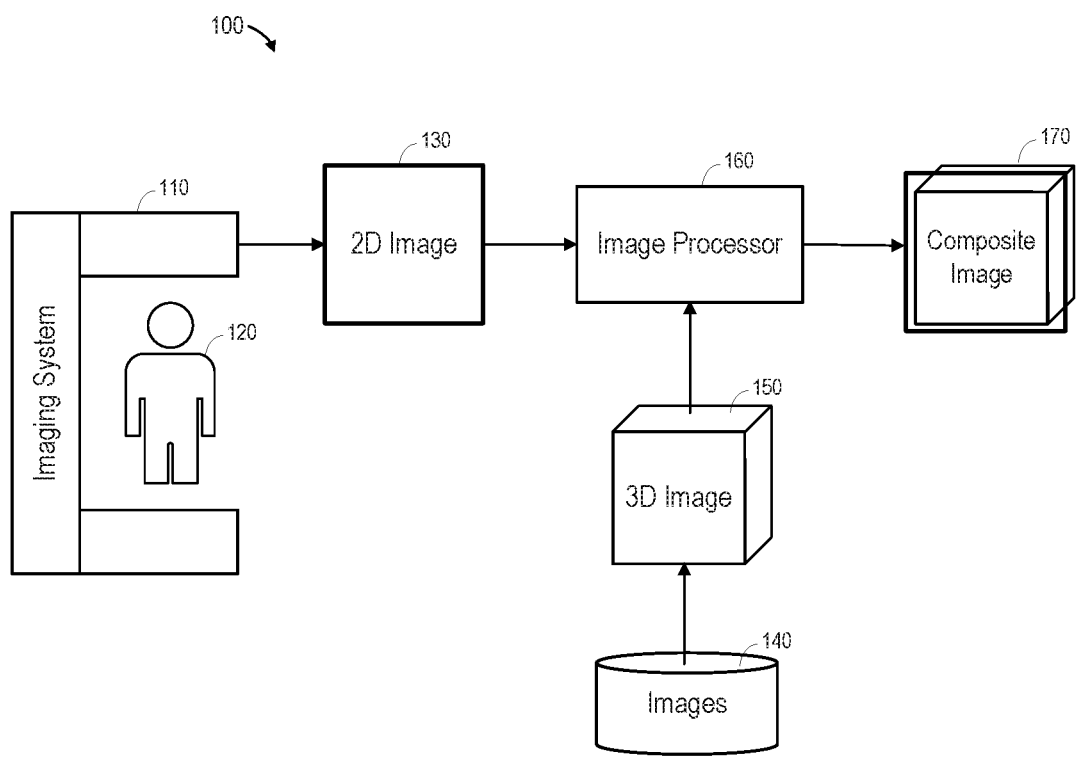
FIG. 1 illustrates processing to generate a composite image according to some embodiments.

The following description is provided to enable any person in the art to make and use the described embodiments and sets forth the best mode contemplated for carrying out the described embodiments. Various modifications, however, will be apparent to those in the art.

Some embodiments facilitate the combination of a two-dimensional image with a three-dimensional image. According to some embodiments, the two-dimensional image (e.g., a two-dimensional angiographic X-ray image) is placed in the three-dimensional image orthogonal to the projection axis of the two-dimensional image. The projection axis may be determined based on the two-dimensional image and/or a position of an imaging system which acquires the two-dimensional image in real-time. In some embodiments, the two-dimensional image is placed at a center of mass of the three-dimensional image. The combined image may be rotated and displayed in three-dimensional space while the two-dimensional image remains at its fixed position relative to the three-dimensional image.

Some embodiments further improve the initial alignment of the two-dimensional image embedded within the three-dimensional image. Briefly, a digitally-reconstructed radiograph (DRR) is derived from the three-dimensional image at the same projection angle as the two-dimensional image. The two-dimensional image is registered to the DRR and is then embedded in the three-dimensional image based on the registration and the depth of the center of mass.

According to some embodiments, the depth at which the two-dimensional image is embedded in the three-dimensional image is based on a location of a region of interest. In this regard, an MPR orthogonal to the projection axis and including the region of interest is determined, and the two-dimensional image is embedded at the depth of the MPR. The two-dimensional image may be further registered with the MPR to improve its rotational and translational registration with the three-dimensional image.

Potential advantages of some embodiments include increased access to relevant anatomical environment information in real-time, a reduced need to acquire an additional three-dimensional image during treatment and the resulting reduction in dose, and improved detection of patient movement.

According to some embodiments, several two-dimensional slice segments (e.g., MPR, Maximum Intensity Profile, Minimum Intensity Profile) are displayed, with an orientation of each segment being orthogonal to the others. A live two-dimensional image is acquired and, in response, the orientation of a displayed two-dimensional slice segment is changed to reflect the projection angle of the live two-dimensional image. The orientations of the other displayed two-dimensional slice segments may also be changed to be orthogonal to the projection angle of the live two-dimensional image.

The live two-dimensional image may also be displayed in combination with a three-dimensional image from which the slice segments were generated, as described above. In such an embodiment, toggling may be provided between the live image and a slice segment having the same angulation. Moreover, controls may be provided to change the relative opacity of each image of the combined three-dimensional, live and slice images.

Some embodiments may therefore assist in visualizing correspondence between a live image and three-dimensional images, particularly in cases where the projection angle of the live image fluctuates.

FIG. 1 is a functional block diagram of system 100 according to some embodiments. Each component of system 100 may be implemented using one or more computing systems, and more than one component may be implemented by a single computing system. Any of the aforementioned computing systems may be located remote from any others.

Generally, imaging system 110 acquires image data representing a volume of patient 120. The image data may be acquired using any imaging modality and in any format that are or become known. Examples include but are not limited to single-photon emission computed tomography (SPECT), positron emission tomography (PET), ultrasound, photoacoustic imaging, magnetic particle imaging, optical coherence tomography, optical camera, infrared camera, three-dimensional camera/depth camera, endoscopy, and digital holographic microscopy.

The image data is processed to generate two-dimensional image 130, using a processing algorithm suitable to the format of the acquired image data. Image 130 may comprise a projection image of patient 120 associated with a projection angle (an angle with respect to the patient of the view depicted in the projection image). Image 130 may include data specifying acquisition parameters (e.g., DICOM data) used to acquire the image data. The parameters may include tube current, source to detector distance, projection angle, and other parameters.

Storage device 140 stores previously-acquired images. The images may include three-dimensional images of patient 120 used to plan treatment or further evaluation of patient 120. The three-dimensional images may be generated based on image data acquired using any of the imaging modalities mentioned above, and using any suitable image reconstruction algorithms. It will be assumed that three-dimensional image 150 depicts an internal volume of patient 120.

In one example, three-dimensional image 150 of patient 120 was previously acquired and segmented to identify anatomical features therein. Image 150 may comprise a magnetic resonance image in a case that the features of interest are soft tissue, and a computed tomography image in a case that the features comprise bone.

Patient 120 is disposed in an imaging position with respect to imaging system 110, which comprises an angiography system in this example. A catheter is inserted into patient 120 and imaging system 110 generates projection image 130 of a volume of patient 120 containing the catheter.

Image processor 160 receives image 130 and three-dimensional image 150 and combines the images. For example, image processor 160 determines a projection angle associated with image 130. The projection angle may be determined from the DICOM data of image 130, by querying imaging system 110 for its current position, or by other means.

Image processor 160 then generates composite image 170 by inserting image 130 into image 150 in an orientation orthogonal to the projection axis. Such insertion requires registering the frame of reference of three-dimensional image 150 to the frame of reference of image 130/system 110 as is known in the art. The depth at which image 130 is placed with three-dimensional image 150 may be determined by determining the center of mass of three-dimensional image 130. More specifically, image 130 may be inserted into image 150 in a plane orientation orthogonal to the projection axis and including the center of mass of image 150.

Figure 2C:
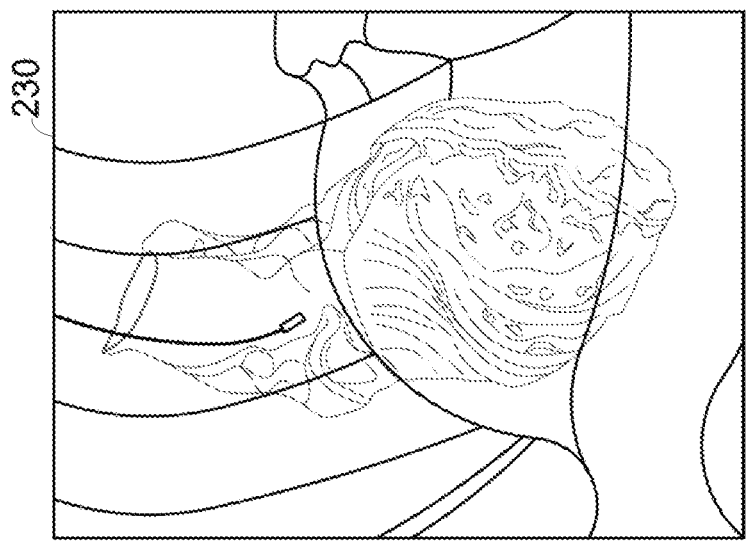
FIG. 2C illustrates a composite image according to some embodiments.
Figure 2B:
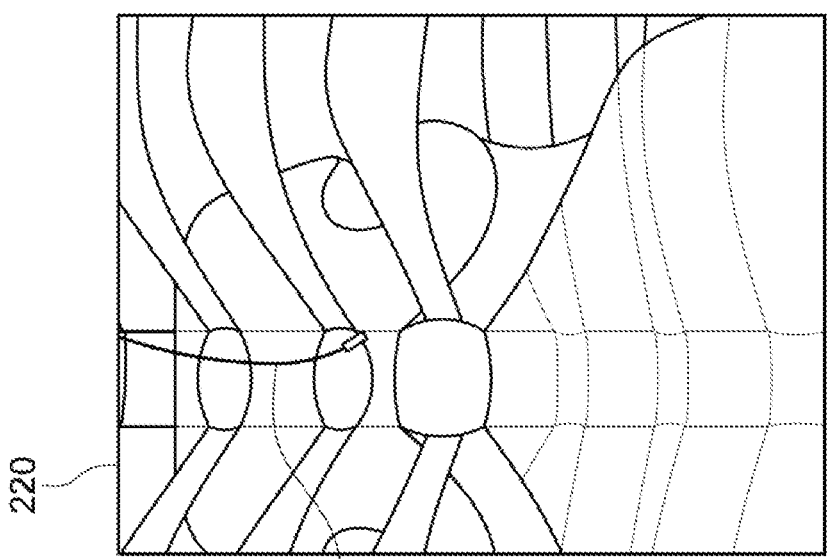
FIG. 2B illustrates a two-dimensional projection image according to some embodiments.
Figure 2A:
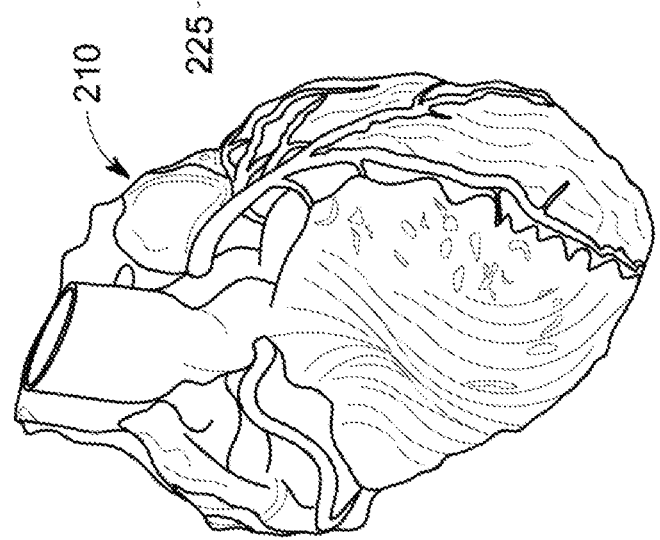
FIG. 2A illustrates a three-dimensional image according to some embodiments.

FIG. 2A illustrates three-dimensional image 210 of a patient volume according to some embodiments. Image 210 may be acquired using any volumetric imaging modality. Two-dimensional image 220 may comprise an angiographic X-ray image of the patient volume. Image 220 depicts catheter 225 within the patient volume. Accordingly, image 220 may be acquired during performance of a medical procedure.

FIG. 2C comprises composite image 230 according to some embodiments. As described above, composite image 230 includes image 220 inserted in a plane of image 210 which is orthogonal to the projection axis of image 220. Moreover, the plane at which image 220 is inserted intersects the center of mass of image 210. As shown in FIG. 2C, the portion of image 210 which is "in front of" image 220 has been made partially transparent. Such transparency allows for viewing of elements of image 220 which are of interest (e.g., catheter 225) but would otherwise be obscured by the portion of image 210. In some embodiments, the portion of image 210 which is "in front of" image 220 is cropped to show a cut plane at the location of the plane in which image 220 is inserted.

Figure 3:
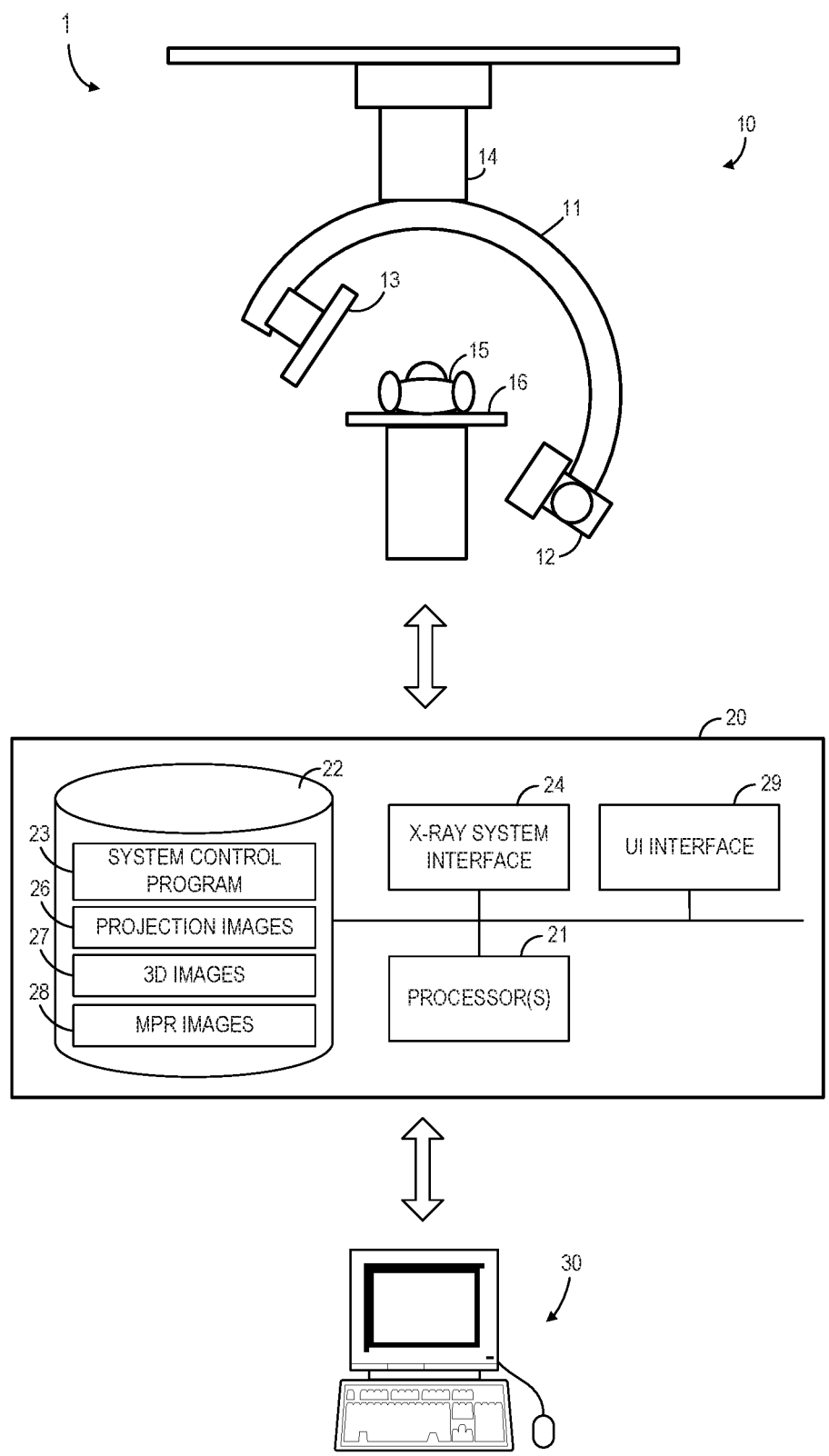
FIG. 3 is a block diagram of an imaging system according to some embodiments.

FIG. 3 illustrates system 1 according to some embodiments. System 1 includes X-ray imaging system 10, control and processing system 20, and operator terminal 30. Generally, and according to some embodiments, X-ray imaging system 10 acquires X-ray image data based on a patient volume. Control and processing system 20 controls X-ray imaging system 10 and receives the acquired image data therefrom. Control and processing system 20 may process the images as described herein and provides the processed images to terminal 30 for display thereby. Such processing may be based on user input received by terminal 30 and provided to control and processing system 20 by terminal 30.

X-ray imaging system 10 comprises C-arm 11 on which radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween. Embodiments are not limited to C-arm-based imaging systems.

Radiation source 12 may comprise any suitable radiation source, including but not limited to an X-ray tube. In some embodiments, radiation source 12 emits electron, photon or other type of radiation having energies ranging from 50 to 150 keV.

Radiation detector 13 may comprise any system to acquire an image based on received X-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by X-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 13 may therefore represent a two-dimensional projection image of these tissues.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to move C-arm 11, to move table 16, to cause radiation source 12 to emit radiation, to control detector 13 to acquire an image, and to perform any other function. In this regard, system 20 includes X-ray system interface 24 for communication with corresponding units of system 10.

Image data acquired from system 10 is stored in data storage device 22 as acquired projection images 26, in DICOM or another data format. Each acquired projection image may be further associated with details of its acquisition, including but not limited to time of acquisition, imaging plane position and angle, imaging position, radiation source-to-detector distance, patient anatomy imaged, patient position, X-ray tube voltage, image resolution and radiation dosage.

Processor(s) 21 may further execute system control program 23 to generate three-dimensional images 27 and MPR images 28 as is known in the art. Any of images 26, 27 and 28, and composite images generated as described herein, may be provided to terminal 30 via UI interface 29 of system 20. UI interface 29 may also receive input from terminal 30, which is used to control generation of composite images as described herein.

Terminal 30 may comprise a display device and an input device coupled to system 20. Terminal 30 displays images received from system 20 and may receive user input for controlling display of the images, operation of imaging system 10, and/or the generation of composite images. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired images being provided to a separate image processing system over a computer network or via a physical storage medium (e.g., a DVD).

Figure 4:
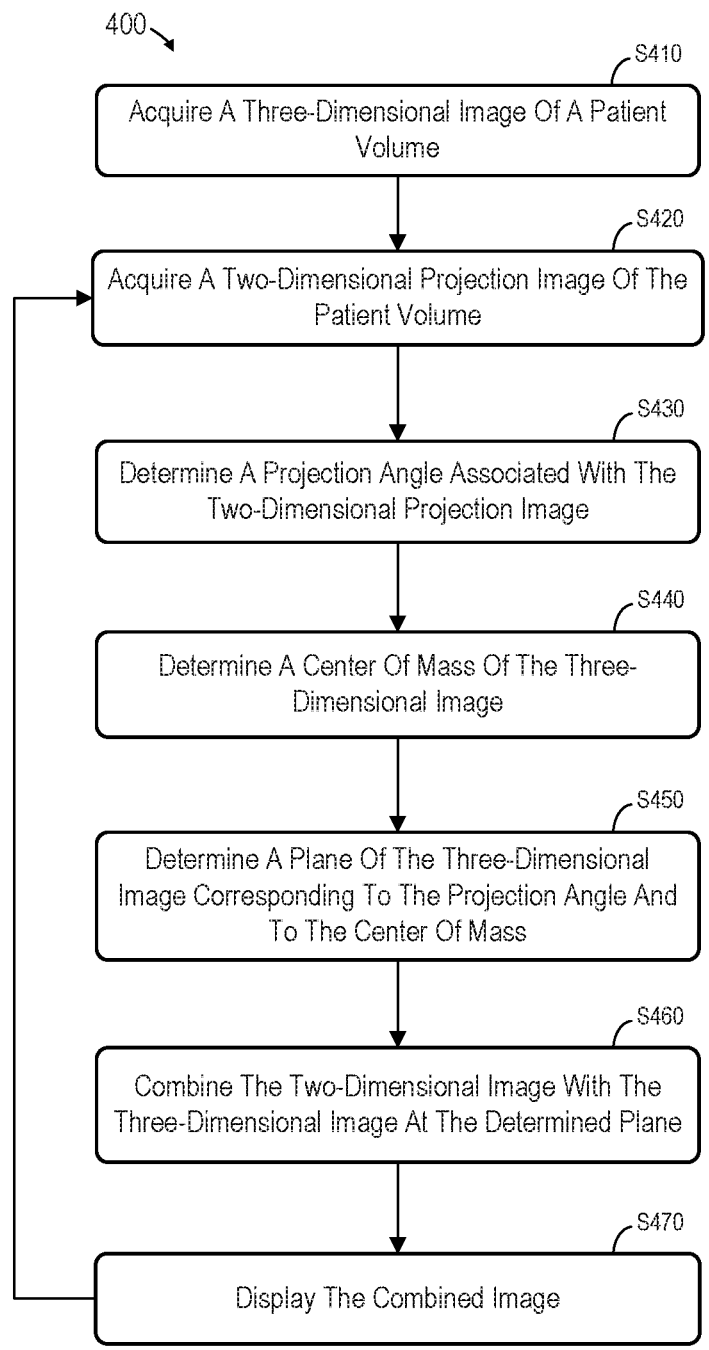
FIG. 4 is a flow diagram of a process to generate a composite image according to some embodiments.

FIG. 4 is a flow diagram of process 400 according to some embodiments. Process 400 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of the system 1, but embodiments are not limited thereto.

Initially, at S10, a three-dimensional image of a patient volume is acquired. The three-dimensional image may be generated and acquired in any manner that is or becomes known. According to some embodiments, the three-dimensional image was generated during a prior image acquisition session, and is acquired at S410 from a data storage device on which the image was stored.

A two-dimensional projection image of the patient volume is acquired at S420. According to some examples, and with reference to the elements of system 1, patient 15 is positioned on table 16 to place a particular volume of patient 15 between radiation source 12 and radiation detector 13. System 20 may assist in adjusting table 16 to position the patient volume as desired. As is known in the art, such positioning may be based on a location of a volume of interest, on positioning markers located on patient 15, on a previously-acquired planning image (e.g., the image acquired at S410), and/or on a portal image acquired after an initial positioning of patient 15 on table 16.

Next, radiation source 12 is powered by a high-powered generator to emit X-ray radiation toward radiation detector 13 at the desired projection angle. The parameters of the X-ray radiation emission (e.g., timing, X-ray tube voltage, dosage) may be controlled by system control program 23 as is known in the art. Radiation detector 13 receives the emitted radiation and produces a set of data (i.e., a projection image). The projection image may be received by system 20 and stored among projection images 26 in either raw form or after any suitable pre-processing (e.g., denoising filters, median filters and low-pass filters).

A projection angle associated with the two-dimensional projection image is determined at S430. As mentioned above, the projection angle may be determined from the DICOM data of image 130, or by querying imaging system 10 for its current position if it has not moved since acquisition of the projection image, for example.

A center of mass of the three-dimensional image is determined at S440 using any suitable algorithm. The determined center of mass may be represented as one or more voxels of the three-dimensional image. Next, at S450, a plane of the three-dimensional image is determined which is orthogonal to the projection axis and includes the determined center of mass. According to some embodiments, the projection axis of the two-dimensional image (which may be defined with respect to imaging system 10) is translated to the image space of the three-dimensional image using known techniques, and the plane is determined with respect to the transformed axis and the location of the center of mass voxels.

The two-dimensional image is combined with the three-dimensional image at the determined plane at S460, and the combined image is displayed (e.g., on terminal 30) at S470. As mentioned above, the three-dimensional image may be cropped by the two-dimensional image at the determined plane (i.e., as a "clip plane") in some embodiments.

In some embodiments, a second two-dimensional image is acquired (e.g., contemporaneously with the first two-dimensional image) at a projection angle different from the projection angle of the first three-dimensional image. The second two-dimensional image may be combined with the three-dimensional image and the first two-dimensional image into the composite image in the same manner as described with respect to the first two-dimensional image.

Figure 5A:
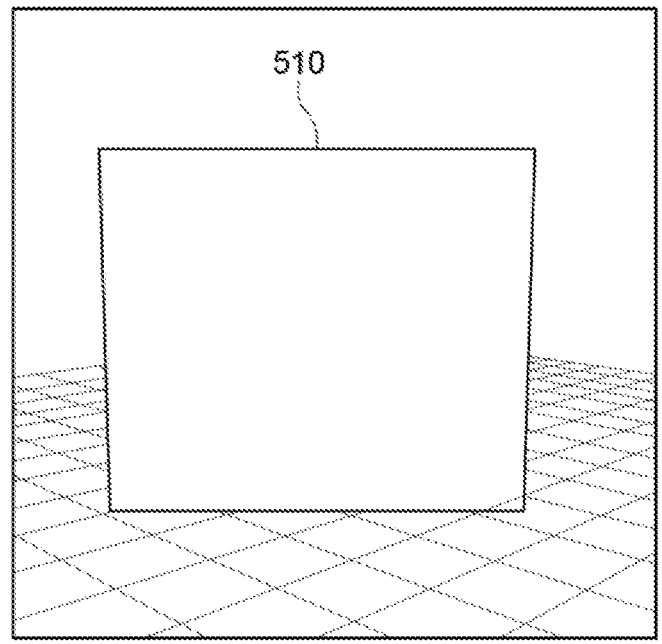
FIG. 5A illustrates a two-dimensional projection image according to some embodiments.
Figure 5B:
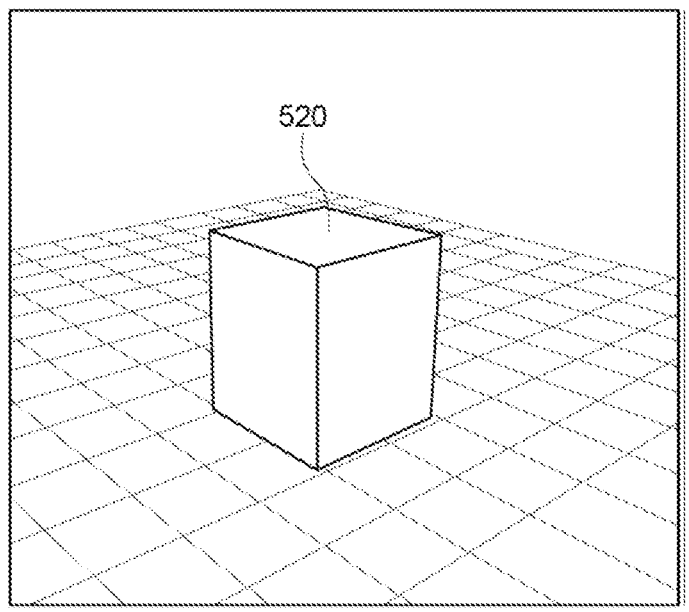
FIG. 5B illustrates a three-dimensional image according to some embodiments.
Figure 5C:
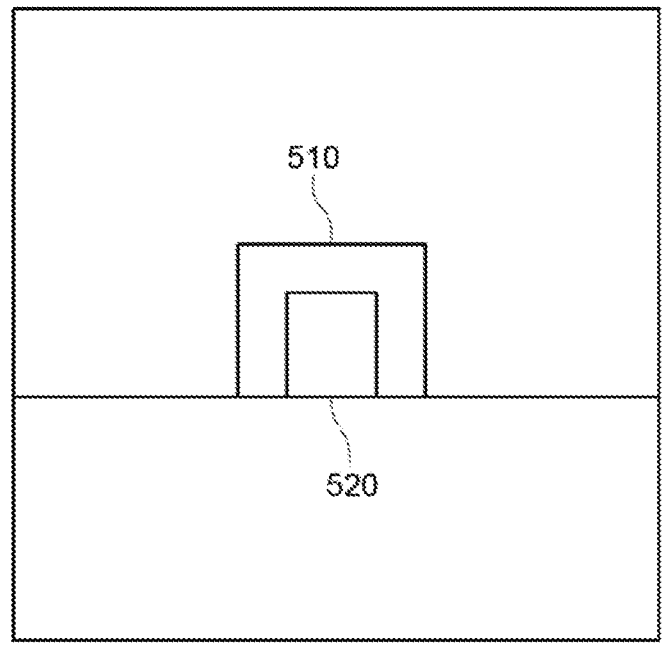
FIG. 5C illustrates a composite image according to some embodiments.
Figure 5D:
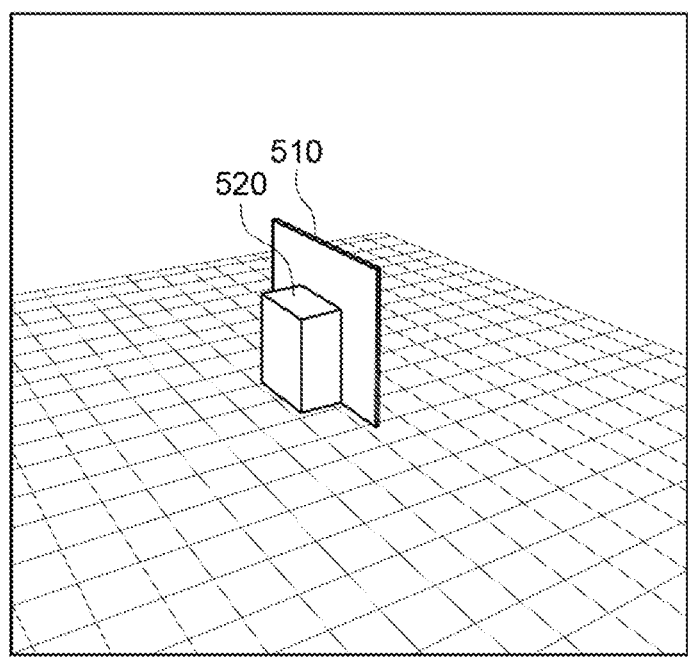
FIG. 5D illustrates a rotated composite image according to some embodiments.

The composite image may be rotated in some embodiments while preserving the relationship between the two-dimensional and three-dimensional images. FIGS. 5A through 5D depict images according to some embodiments. FIG. 5A depicts two-dimensional image 510 and FIG. 5B depicts three-dimensional image 520. FIG. 5C shows image 510 combined with image 520 as described above. The combined images may be rotated as shown in FIG. 5D. Specifically, image 510 remains in a fixed plane of image 520 while the combined images are rotated, thereby providing additional detail of the relationship therebetween.

Flow may return from S470 to S420 to provide live updates according to some embodiments. More specifically, after display of the combined image at S470, another two-dimensional projection image may be obtained at S420. This next two-dimensional image may be acquired from the same or a different projection angle than the previously-acquired two-dimensional image. If the projection angle is the same, the next two-dimensional image is combined with the three-dimensional image at the previously-determined plane at S460. If the projection angle is different, a next plane is determined at S450 based on the different projection angle and the center of mass, and the next two-dimensional image is combined with the three-dimensional image at the newly-determined plane at S460.

According to the examples described above with respect to FIGS. 1 through 5, the two-dimensional image is typically well-aligned with the determined plane of the three-dimensional image if the three-dimensional image was acquired by the same system used to acquire the two-dimensional image. However, it is possible, particularly if different imaging systems are used to acquire the images, that the two-dimensional image will be translationally and/or rotationally misaligned with the determined plane of the three-dimensional image when combined with the three-dimensional image.

Figure 6:
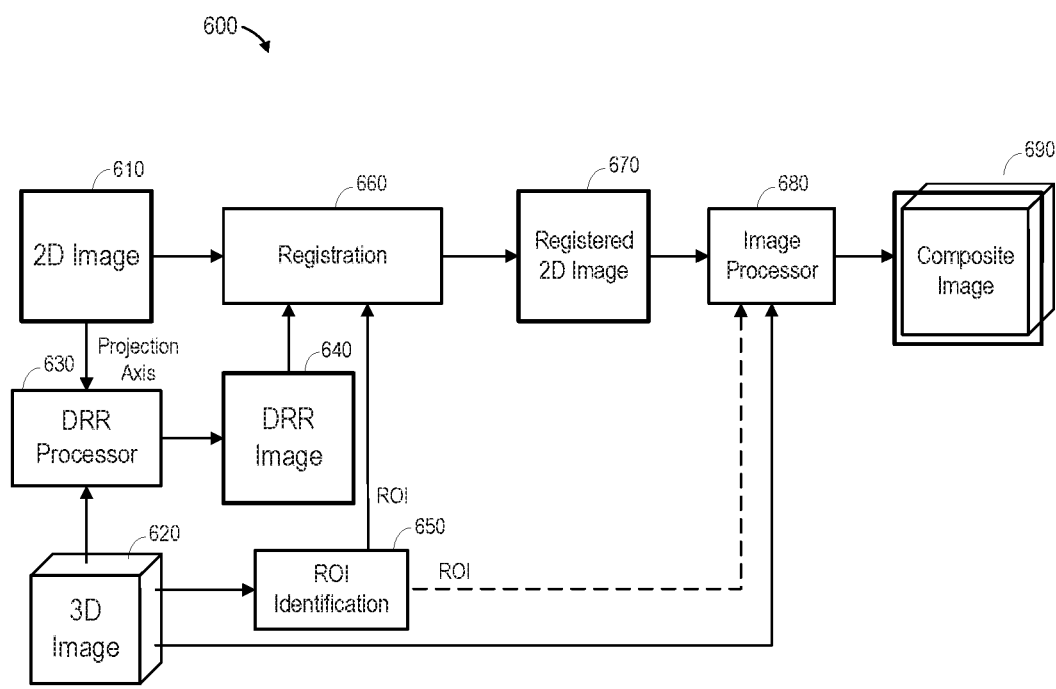
FIG. 6 illustrates processing to generate a composite image according to some embodiments.

FIG. 6 illustrates an embodiment of process 600 to improve the alignment between the determined plane of the three-dimensional image and the two-dimensional image which is inserted at the determined plane.

Two-dimensional image 610, as described above with respect to two-dimensional image 130 may comprise a projection image of a patient which is associated with a projection angle. Three-dimensional image 620 may comprise a magnetic resonance image, a computed tomography image, or other three-dimensional image of the patient. As shown, images 610 and 620 are received by DRR processor 630.

DRR processor 630 derives two-dimensional digitally-reconstructed radiograph (DRR) image 640 from three-dimensional image 620 at the same projection angle as two-dimensional image 610. Region of interest (ROI) component 650 identifies an ROI within three-dimensional image 620, automatically and/or in conjunction with operator input. Registration component 660 registers two-dimensional image 610 with DRR image 640 at the ROI using known registration techniques, including but not limited to landmark detection within each image.

Image processor 680 combines registered two-dimensional image 670 and three-dimensional image 620 to create composite image 690. According to some embodiments, registered two-dimensional image 670 is embedded in three-dimensional image 620 at a plane orthogonal to the projection axis and including the center of mass of three-dimensional image 620. These embodiments may provide suitable alignment between two-dimensional image 670 and three-dimensional image 620 in which image 670 is embedded.

In some embodiments, image processor 680 receives an indication of the ROI and embeds registered two-dimensional image 670 at a plane orthogonal to the projection axis and including the ROI. Since two-dimensional image 610 is registered with DRR image 640 at the ROI, these embodiments may provide improved alignment between two-dimensional image 670 and three-dimensional image 620 in which image 670 is embedded.

Figure 7A:
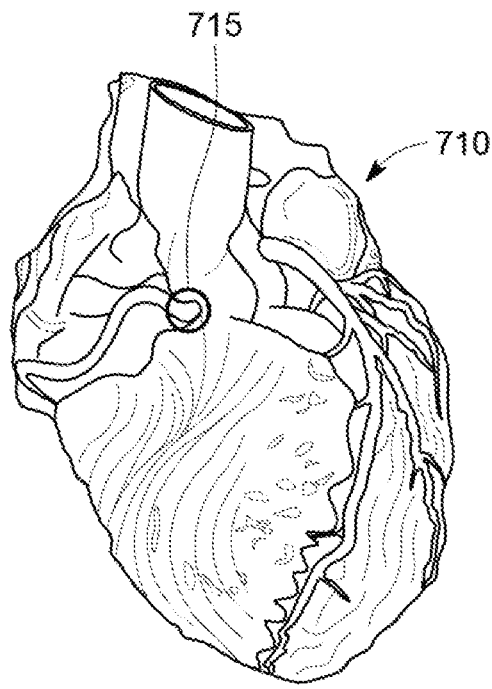
FIG. 7A illustrates a three-dimensional image according to some embodiments.
Figure 7B:
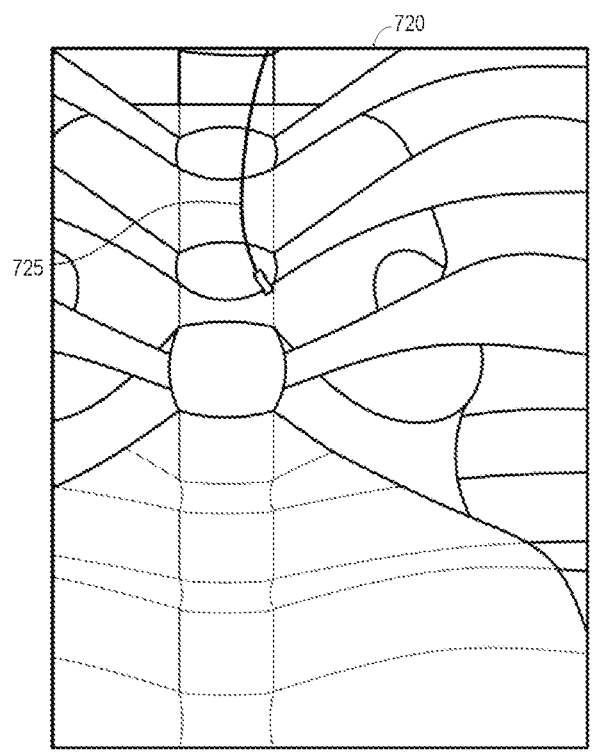
FIG. 7B illustrates a two-dimensional projection image according to some embodiments.

FIG. 7A illustrates three-dimensional image 710 of a patient volume according to some embodiments. ROI 715 has been selected in image 710 by an operator, for example. FIG. 7B shows two-dimensional X-ray image 720, depicting catheter 725 as described with respect to FIG. 2B.

Figure 7C:
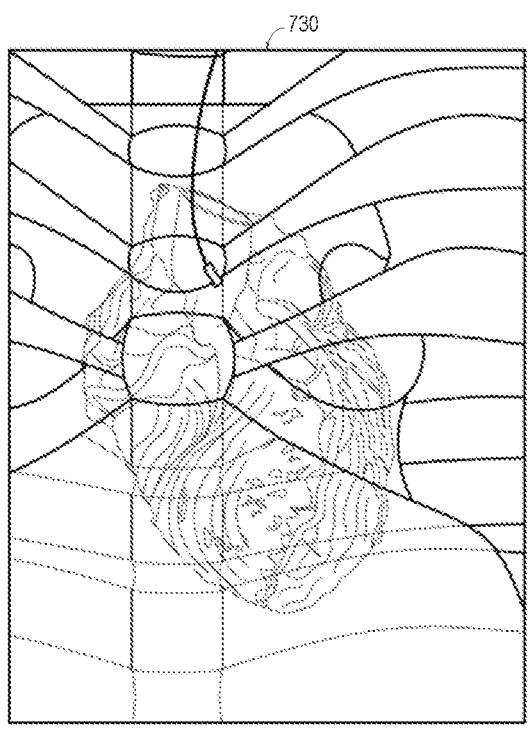
FIG. 7C illustrates a Digitally-Reconstructed Radiograph image according to some embodiments.

FIG. 7C comprises DRR image 730 generated based on image 710 as is known in the art. Image 730 is associated with a same projection angle as image 720, therefore their depicted structures are similar. DRR image 730 may be generated in view of the source, detector, and isocenter geometry used to acquire image 720, thereby increasing the similarities between images 720 and 730 and facilitating registration therebetween.

Figure 7D:
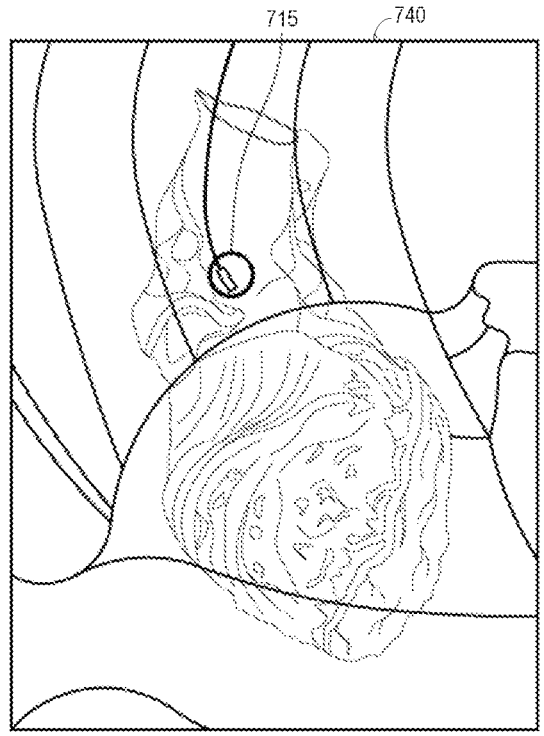
FIG. 7D illustrates a composite image showing a region of interest according to some embodiments.

Lastly, FIG. 7D depicts composite image 740 including image 720 embedded at a plane of three-dimensional image 710. As mentioned above, image 720 is embedded at a plane orthogonal to the projection axis and including ROI 715. As also mentioned above, composite image 740 may show three-dimensional image 710 clipped, or cut away, by image 720 at the plane.

Figure 8:
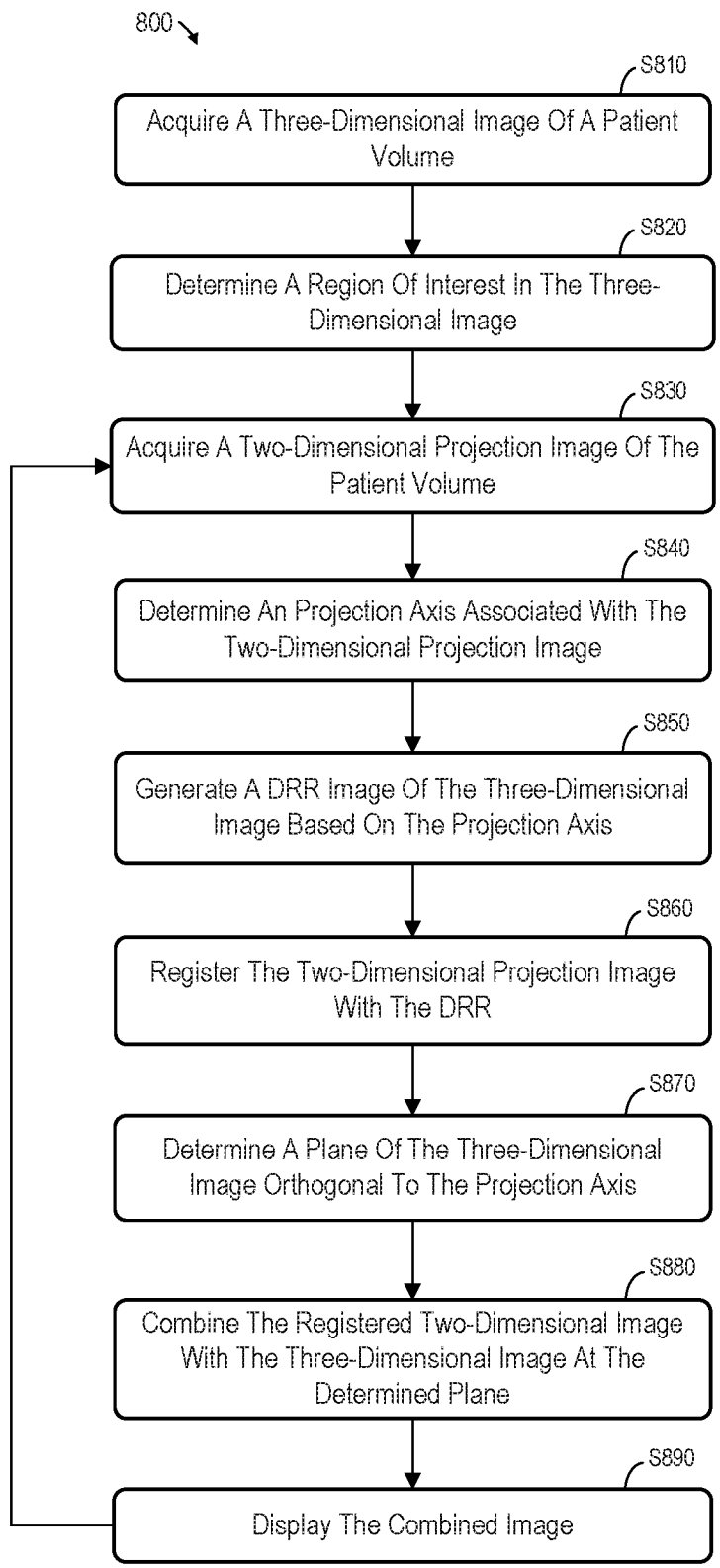
FIG. 8 is a flow diagram of a process to generate a composite image according to some embodiments.

FIG. 8 is a flow diagram of process 800 according to some embodiments. Process 800 may be implemented as described with respect to system 600 of FIG. 6, but embodiments are not limited thereto. A three-dimensional image of a patient volume is initially acquired at S810. The three-dimensional image may have been acquired and generated during a prior image acquisition session.

A region of interest within the three-dimensional image is determined at S820. In some embodiments of S820, the three-dimensional image is displayed on a display device and an operator manipulates an input device to select a region of interest within the displayed three-dimensional image. For example, the operator may operate a mouse to draw a circle or sphere around a volume of interest. To facilitate selection of the region of interest, the three-dimensional image may be segmented prior to S820 to identify various structures and boundaries depicted therein and the structures/boundaries may be accentuated in the displayed image.

A two-dimensional projection image of the patient volume is then acquired at S830, and a projection axis associated with the two-dimensional projection image is determined at S840.

At S850, a DRR image of the three-dimensional image is generated. The DRR image is generated based on the projection axis of the two-dimensional projection image. As mentioned above, the DRR image may be generated in view of the source, detector, and isocenter geometry used to acquire the two-dimensional projection image at S830. The two-dimensional image is registered against the DRR image 640 at S860. Registration may include the identification of similar anatomical landmarks and/or surface markers within each image and generation of a transformation matrix based on the location of the landmarks and/or markers within each image. Registration may be rigid or flexible as is known in the art. According to some embodiments, registration is performed with emphasis on achieving accurate registration between the regions of each image which include the ROI.

Next, at S870, a plane of the three-dimensional image is determined which is orthogonal to the projection axis. The depth of the plane within the three-dimensional image may be selected so as to include the center of mass. In some embodiments, the determined plane is orthogonal to the projection axis and includes the ROI. The determination at S870 may therefore include determination of an MPR of the three-dimensional image which is orthogonal to the projection axis and includes the ROI, and determination of a plane within the MPR.

The registered two-dimensional image is combined with the three-dimensional image at the determined plane at S880, and the combined image is displayed at S890. As described above with respect to process 400, flow may return from S890 to S830 to acquire another two-dimensional projection image. This next two-dimensional image may be acquired from the same or a different projection angle than the previously-acquired two-dimensional image. If the projection angle is the same, the next two-dimensional image is combined with the three-dimensional image at the previously-determined plane at S880. If the projection angle is different, a next plane is determined at S870 based on the different projection angle and the center of mass or ROI, and the next two-dimensional image is combined with the three-dimensional image at the newly-determined plane at S880.

Figure 9:
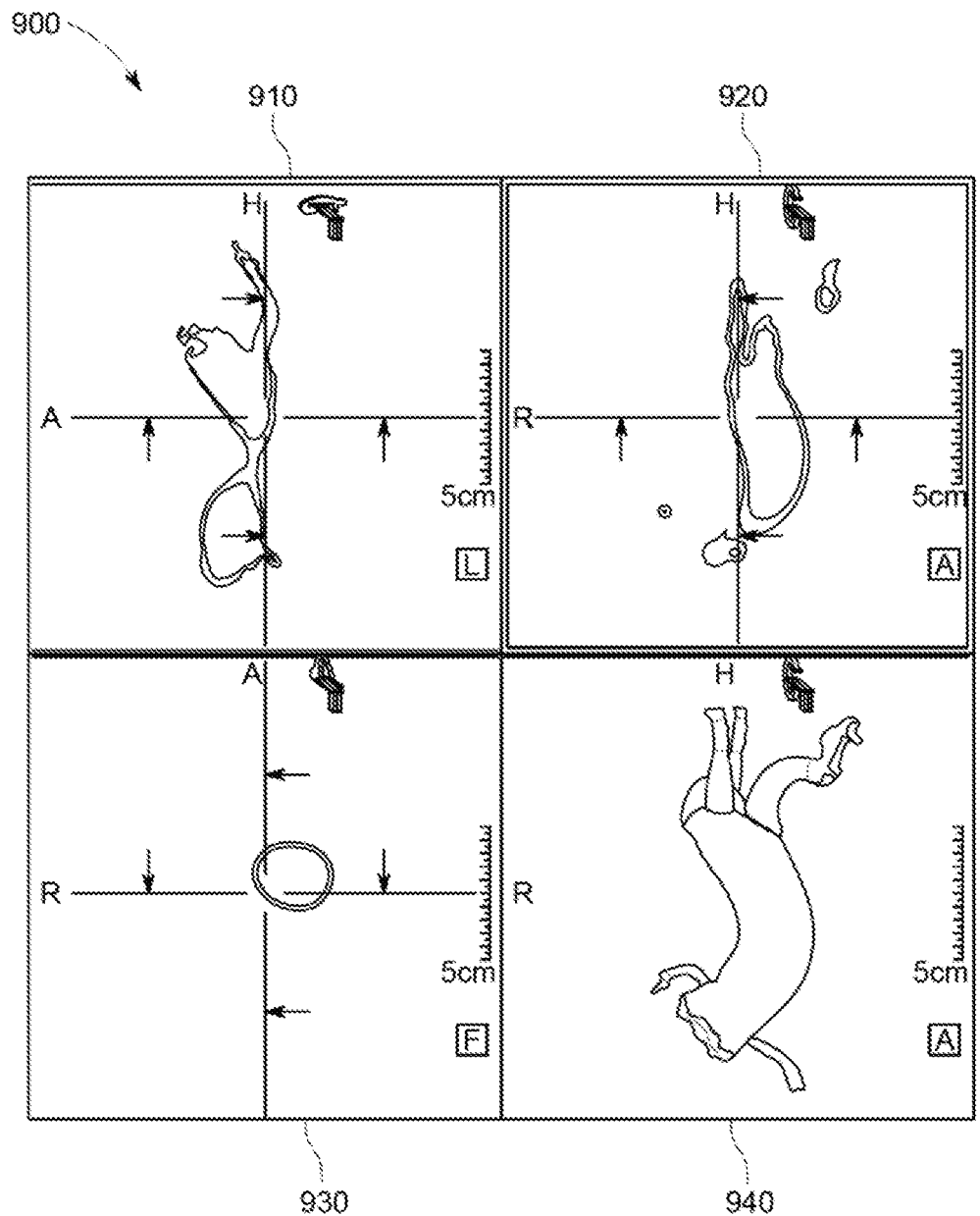
FIG. 9 depicts a plurality of image slices generated according to some embodiments.

FIG. 9 illustrates display 900 including four display areas 910 through 940. As is known in the art, each of areas 910, 920 and 930 displays a slice image taken from the three-dimensional volume displayed in area 940. Each slice image represents a plane of the three-dimensional volume, and each of the three represented planes is orthogonal to the other two represented planes. According to typical usage, the planes may be sagittal, coronal and axial anatomical planes.

Figure 10:
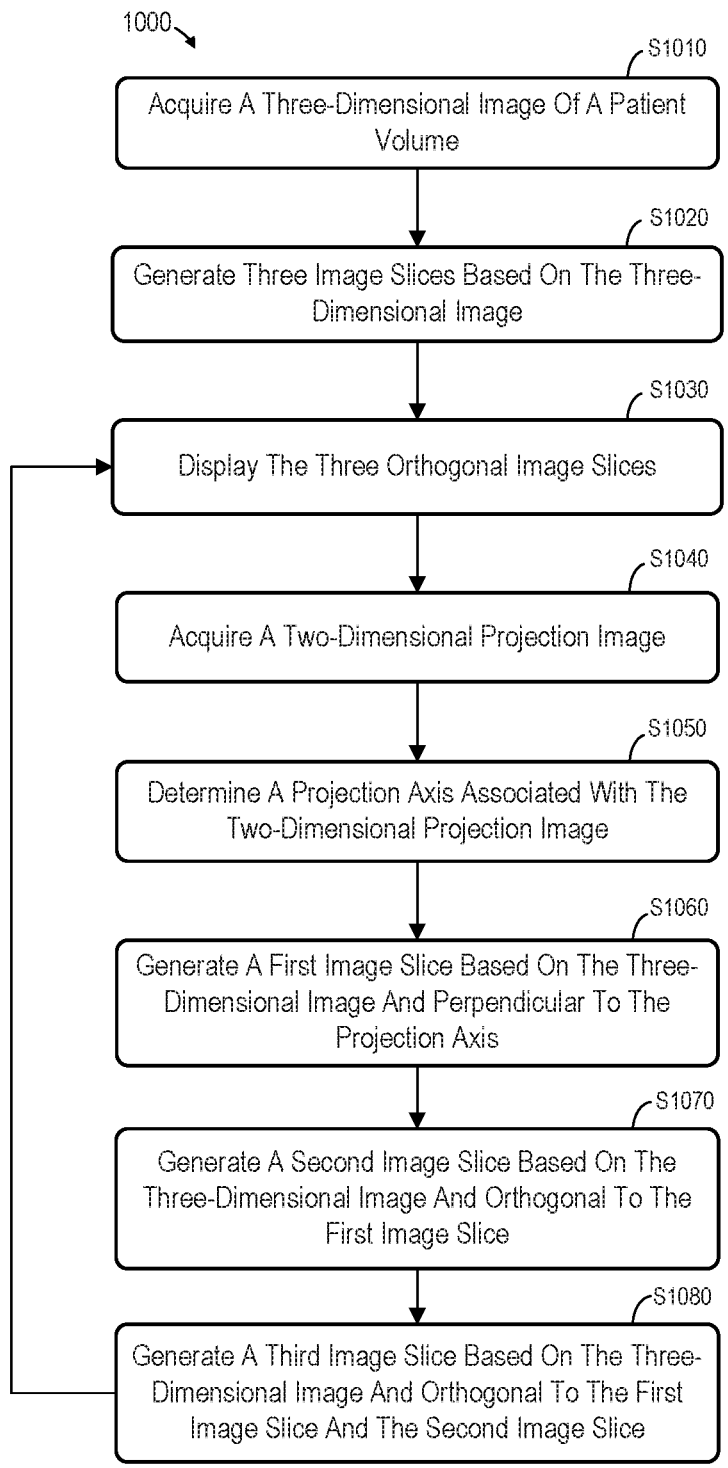
FIG. 10 is a flow diagram of a process to determine, generate and display a plurality of image slices according to some embodiments.

FIG. 10 is a flow diagram of process 1000 to supplement a display such as display 900 according to some embodiments. As has been described, a three-dimensional image of a patient volume is acquired at S1010. Three image slices (e.g., MPR, Maximum Intensity Profile, Minimum Intensity Profile) are generated from the three-dimensional image at S1020 as is known in the art. Each of the image slices is orthogonal to the others.

Each image slice is displayed at S1030, for example as shown in FIG. 9. Embodiments are not limited to the appearance and/or configuration of display 900.

A two-dimensional projection image is acquired at S1040. As described herein, the three-dimensional image may be a planning image acquired during a previous imaging session (e.g., on a previous day), while the two-dimensional projection image may be acquired at S1040 by an imaging device immediately prior to execution of the remaining steps of process 1000.

A projection axis of the acquired two-dimensional projection image is determined at S1050, and a first image slice of the three-dimensional image is generated at S1060. The first image slice is perpendicular to the projection axis. A depth of the slice may be based on the center of mass of the three-dimensional image, a region of interest of the three-dimensional image, and/or on any other criteria.

A second image slice of the three-dimensional image is generated at S1070. The plane of the second image slice is orthogonal to the plane of the first image slice. Next, at S1080, a third image slice of the three-dimensional image is generated, with a plane of the third image slice being orthogonal to the plane of the first image slice and the plane of the second image slice. Flow returns to S1030 to display the newly-generated three orthogonal image slices and continues as described above.

Therefore, if a next two-dimensional projection image is acquired at S1040 from a new projection angle, the three slice images subsequently-generated at S1060, S1070 and S1080 will (if the new projection axis is not orthogonal to the last projection axis) represent three different planes of the three-dimensional image. Accordingly, process 1000 provides updating of the planes of the displayed slice images based on a projection axis of the image acquired at S1040.

Figure 11:
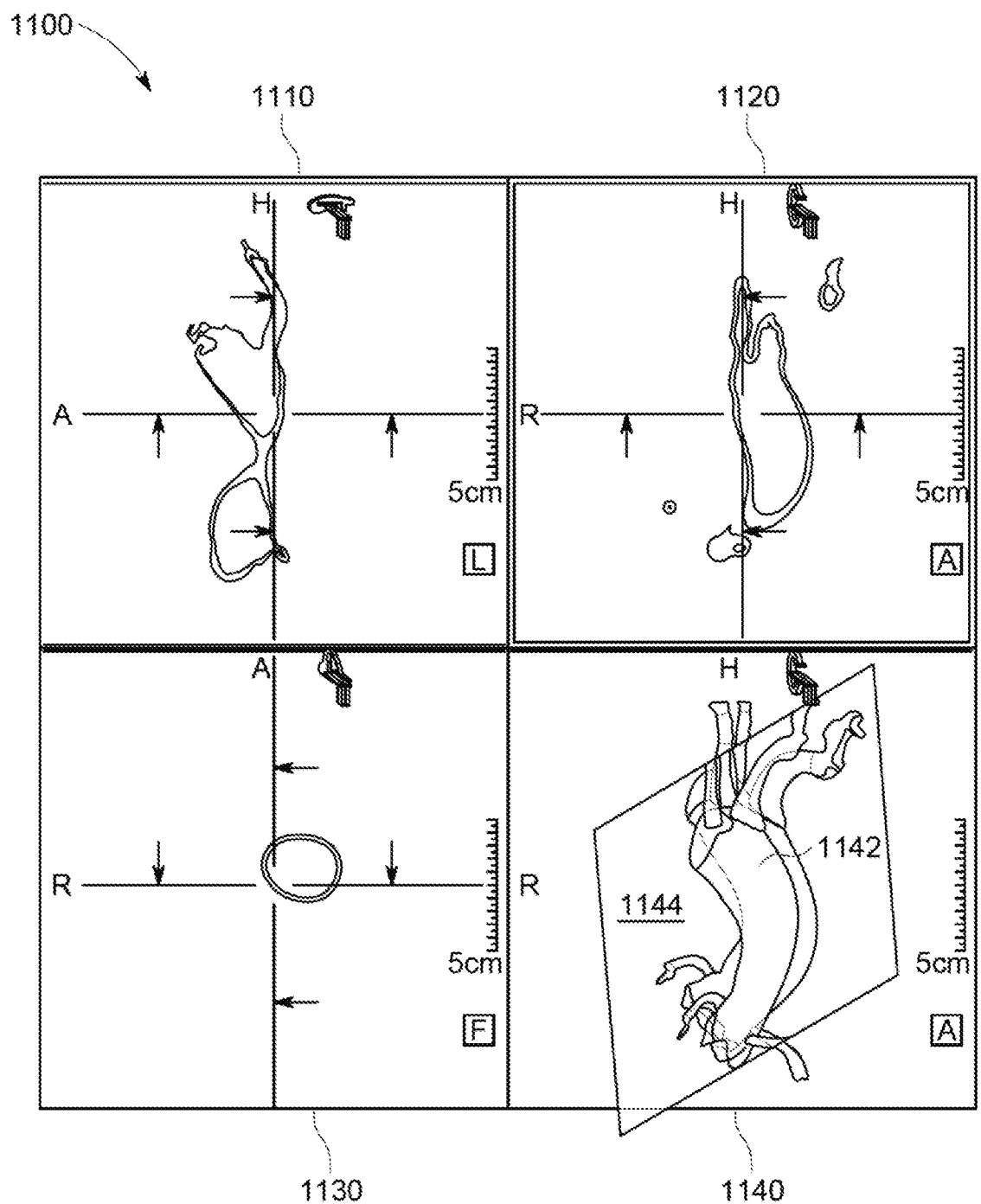
FIG. 11 depicts a plurality of image slices and a composite image generated according to some embodiments.

FIG. 11 illustrates an embodiment in which display area 1140 includes three-dimensional image 1142 from which the slice images of display areas 1110, 1120 and 1130 were generated. Also shown in area 1140 is two-dimensional image 1144 acquired at S1040 and combined with image 1142 in any manner described herein or otherwise. According to the FIG. 11 embodiment, acquisition of a next two-dimensional image not only causes updating of the planes of the slice images shown in areas 1110, 1120 and 1130, but also causes combination of the next two-dimensional image with the three-dimensional image and display of the newly-combined image in area 1140.

Figure 12:
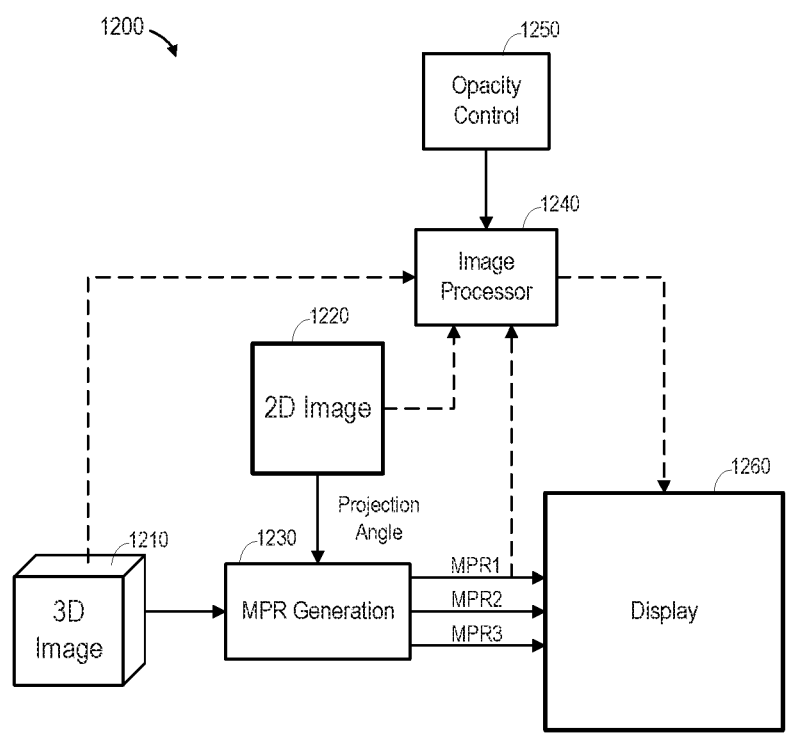
FIG. 12 illustrates processing to display a plurality of image slices and a composite image according to some embodiments.

FIG. 12 is a block diagram of system 1200 implementing process 1100 according to some embodiments. As described above, three-dimensional image 1210 and two-dimensional image 1220 are acquired and a projection angle of two-dimensional image 1220 is determined. MPR generation component 1230 generates three MPR images (MPR1, MPR2 and MPR3) based on the projection angle. Specifically, component 1230 generates one MPR image slice (e.g., MPR1) of three-dimensional image 1210 in a plane orthogonal to a projection axis corresponding to the projection angle, and two other MPR image slices (e.g., MPR2 and MPR3) of three-dimensional image 1210 in planes orthogonal to the plane of the first MPR slice and to each other. Display 1260 displays the three image slices as described above.

The dashed lines of FIG. 12 indicate the optional combination and display of three-dimensional image 1210 and two-dimensional image 1220 according to some embodiments. Image processor 1240 may receive images 1210 and 1220 and combine the images as described above with respect to processes 400 and 800. Image processor 1240 may also receive slice image MPR1, which is coplanar to the plane of three-dimensional image 1210 in which two-dimensional image 1220 is embedded. Image processor 1240 may receive operator commands to toggle between combination and display of two-dimensional image 1220 and three-dimensional image 1210, and combination and display of slice image MPR1 and three-dimensional image 1210.

System 1200 also includes opacity control 1250. Opacity control 1250 may indicate a relative opacity of each of images 1210 and 1220 in the combined image. If the combined image includes slice image MPR1 and three-dimensional image 1210, opacity control 1250 may indicate a relative opacity of each of these images. Image processor 1240 uses the indicated opacity to inform generation of the composite image which is displayed on display 1260.

Figure 13:
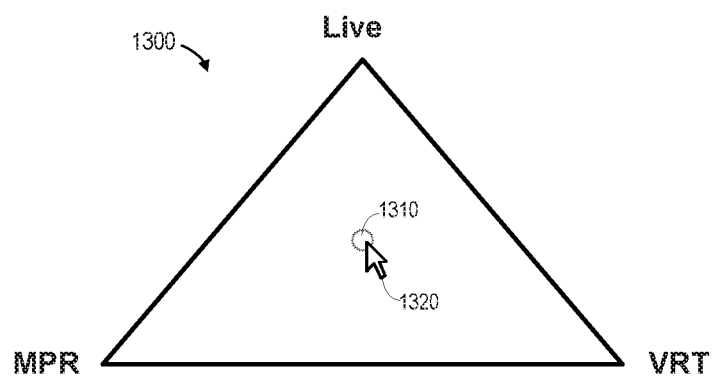
FIG. 13 illustrates a user interface control according to some embodiments.

FIG. 13 illustrates opacity control 1300 according to some embodiments. Opacity control 1300 may be manipulated by an operator in order to control a relative opacity of a two-dimensional image (i.e., Live), an image slice (i.e., MPR), and a three-dimensional image (i.e., VRT) in a composite image generated by image processor 1240. In some embodiments, an operator uses cursor 1320 to select and drag icon 1310 to various locations of the illustrated triangle. Each vertex corresponds to maximum opacity of the associated image, while the center of the triangle is associated with equal opacity of all images. By controlling relative opacity, control also allows an operator to toggle between display of any one or two of the three images within the composite image.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
   a storage device to store:
   a two-dimensional projection image of internal structures of a patient volume; and
   a three-dimensional image of the internal structures of the patient volume;
   a processor to:
   determine a projection axis associated with the two-dimensional projection image;
   generate a two-dimensional image of the internal structures of the patient volume from the three-dimensional image based on the projection axis;
   register the two-dimensional projection image with the two-dimensional image;
   determine a plane of the three-dimensional image which is substantially orthogonal to the projection axis and includes a region of interest of the patient volume;
   generate a combined image by inserting the registered two-dimensional projection image in the plane of the three-dimensional image, which is substantially orthogonal to the projection axis and includes the region of interest of the patient volume, and inserting the two-dimensional image in the plane of the three-dimensional image, which is substantially orthogonal to the projection axis and includes the region of interest of the patient volume;
   receive an instruction to change a first opacity of the two-dimensional projection image, a second opacity of the three-dimensional image, a third opacity of the two-dimensional image in the combined image; and
   in response to the instruction, change the first opacity of the two-dimensional projection image, the second opacity of the three-dimensional image, and the third opacity of the two-dimensional image in the combined image to generate a second combined image, wherein the changed first opacity is different from the changed second opacity and the changed third opacity is different from the changed first opacity and the change second opacity; and
   a display to display the combined image and the second combined image.

2. The system according to claim 1, wherein the two-dimensional image comprises a digitally-reconstructed radiographic image.

3. The system according to claim 1, the processor further to:
   determine a location of a center of mass of the three-dimensional image; and
   determine the plane of the three-dimensional image to include the location of the center of mass.

4. The system according to claim 1, wherein determination of the plane comprises determination of a two-dimensional slice image of the three-dimensional image which includes the region of interest, and determination of the plane within the two-dimensional slice image.

5. The system according to claim 1,
   wherein the two-dimensional projection image is registered with the two-dimensional image at the region of interest.

6. A method comprising:
   acquiring a three-dimensional image of internal structures of a patient volume;
   acquiring a two-dimensional projection image of the internal structures of the patient volume;
   determining a projection axis associated with the two-dimensional projection image;
   generating a two-dimensional image from the three-dimensional image associated with the projection axis;
   aligning the two-dimensional projection image with the two-dimensional image;
   determining a plane of the three-dimensional image which is substantially orthogonal to the projection axis and includes a region of interest of the patient volume;
   generating a combined image by combining the aligned two-dimensional projection image with the three-dimensional image to embed the aligned two-dimensional projection image in the plane of the three-dimensional image, which is substantially orthogonal to the projection axis and includes the region of interest of the patient volume, and inserting the two-dimensional image in the plane of the three-dimensional image, which is substantially orthogonal to the projection axis and includes the region of interest of the patient volume;
   displaying the combined image;
   receiving an instruction to change a first opacity of the two-dimensional projection image, a second opacity of the three-dimensional image, and a third opacity of the two-dimensional image in the combined image;
   in response to the instruction, changing the first opacity of the two-dimensional projection image, the second opacity of the three-dimensional image, and the third opacity of the two-dimensional image in the combined image to generate a second combined image, wherein the changed first opacity is different from the changed second opacity and the changed third opacity is different from the changed first opacity and the changed second opacity; and displaying the second combined image.

7. The method according to claim 6, further comprising:

acquiring a second two-dimensional projection image of the patient volume;

determining a second projection axis associated with the second two-dimensional projection image, the second projection axis different from the projection axis;

generating a second two-dimensional image from the three-dimensional image associated with the second projection axis;

aligning the second two-dimensional projection image with the second two-dimensional image;

combining the aligned second two-dimensional projection image with the three-dimensional image to generate a third combined image in which the aligned second two-dimensional projection image is embedded in a second plane of the three-dimensional image substantially orthogonal to the second projection axis and including the region of interest of the patient volume; and displaying the third combined image.

8. The method according to claim 6, further comprising:

determining a location of a center of mass of the three-dimensional image; and determining the plane of the three-dimensional image to include the location of the center of mass.

9. The method according to claim 6, wherein determining the plane comprises determining a two-dimensional slice image of the three-dimensional image which includes the region of interest, and determining the plane within the two-dimensional slice image.

10. The method according to claim 6, wherein the two-dimensional projection image is aligned with the two-dimensional image at the region of interest.

11. A system comprising:

an X-ray detector and an X-ray source operable to:
acquire a two-dimensional projection image of internal structures of a patient volume;

a computing system to:
determine a projection axis associated with the two-dimensional projection image;
generate a two-dimensional image of the internal structures of the patient volume from a stored three-dimensional image of the internal structures of the patient volume based on the projection axis;
register the two-dimensional projection image with the two-dimensional image;
determine a plane of the three-dimensional image which is substantially orthogonal to the projection axis and includes a region of interest of the patient volume;
generate a combined image by combining the registered two-dimensional projection image with the three-dimensional image to embed the registered two-dimensional projection image in the plane of the three-dimensional image, which is substantially orthogonal to the projection axis and includes the region of interest of the patient volume, and combining the two-dimensional image in the plane of the three-dimensional image, which is substantially orthogonal to the projection axis and includes the region of interest of the patient volume;
receive an instruction to change a first opacity of the two-dimensional projection image, a second opacity of the three-dimensional image, and a third opacity of the two-dimensional image in the combined image; and
in response to the instruction, change the first opacity of the two-dimensional projection image, the second opacity of the three-dimensional image, and the third opacity of the two-dimensional image in the combined image to generate a second combined image, wherein the changed first opacity is different from the changed second opacity and the changed third opacity is different from the changed first opacity and the changed second opacity; and a display to display the combined image and the second combined image.

12. The system according to claim 11, wherein the two-dimensional image comprises a digitally-reconstructed radiographic image.

13. The system according to claim 11, the computing system further to:

determine a location of a center of mass of the three-dimensional image; and determine the plane of the three-dimensional image to include the location of the center of mass.

14. The system according to claim 11, wherein the two-dimensional projection image is registered with the two-dimensional image at the region of interest.

15. The system according to claim 11, wherein determination of the plane comprises determination of a two-dimensional slice image of the three-dimensional image which includes the region of interest, and determining the plane within the two-dimensional slice image.

* * * * *